United States Patent
Douthat et al.

(10) Patent No.: US 10,687,789 B1
(45) Date of Patent: Jun. 23, 2020

(54) METHOD AND SYSTEM FOR RECONSTRUCTING A THERMOACOUSTIC IMAGE

(71) Applicant: ENDRA Life Sciences Inc., Ann Arbor, MI (US)

(72) Inventors: Dean Zahn Douthat, Saline, MI (US); Jang Hwan Cho, Ann Arbor, MI (US); Michael M. Thornton, London (CA)

(73) Assignee: ENDRA Life Sciences Inc., Ann Arbor, MI (US)

( * ) Notice: Subject to any disclaimer, the term of this patent is extended or adjusted under 35 U.S.C. 154(b) by 0 days.

(21) Appl. No.: 16/279,626

(22) Filed: Feb. 19, 2019

(51) Int. Cl.
*A61B 8/08* (2006.01)
*A61B 5/00* (2006.01)
*A61B 8/00* (2006.01)

(52) U.S. Cl.
CPC .......... *A61B 8/5207* (2013.01); *A61B 5/0093* (2013.01); *A61B 5/7203* (2013.01); *A61B 5/7225* (2013.01); *A61B 8/58* (2013.01)

(58) Field of Classification Search
None
See application file for complete search history.

(56) References Cited

U.S. PATENT DOCUMENTS

| | | |
|---|---|---|
| 4,197,750 A | 4/1980 | Hassler |
| 6,497,666 B1 | 12/2002 | Phillips et al. |
| 6,567,688 B1 | 5/2003 | Wang |
| 7,867,166 B2 | 1/2011 | Waag et al. |
| 9,538,987 B2 | 1/2017 | Hoctor et al. |
| 9,700,284 B2 | 7/2017 | Kapoor et al. |
| 2010/0298689 A1 | 11/2010 | Wang |
| 2012/0123256 A1* | 5/2012 | Razansky ............ A61B 5/0095 600/431 |
| 2013/0304405 A1* | 11/2013 | Schmid .................. G01H 1/003 702/56 |
| 2014/0247456 A1 | 9/2014 | Horstmann et al. |
| 2015/0289847 A1 | 10/2015 | Park et al. |
| 2016/0095520 A1 | 4/2016 | Zhang et al. |
| 2017/0032519 A1* | 2/2017 | Thornton ............. A61B 8/4416 |

* cited by examiner

*Primary Examiner* — Pascal M Bui Pho
*Assistant Examiner* — Farouk A Bruce
(74) *Attorney, Agent, or Firm* — Stanley E. Jelic

(57) ABSTRACT

A method and system for reconstructing a thermoacoustic image that utilizes the steps of directing radio frequency (RF) energy pulses generated by an RF source into a tissue region of interest; detecting, at each of a plurality of views along a scanning trajectory of a transducer element array about the region of interest, acoustic signals generated within the region of interest in response to the RF energy pulses and generating thermoacoustic data; applying at least one correction kernel to the thermoacoustic data; and after the at least one correction kernel has been applied to the thermoacoustic data, reconstructing a thermoacoustic image therefrom.

16 Claims, 8 Drawing Sheets

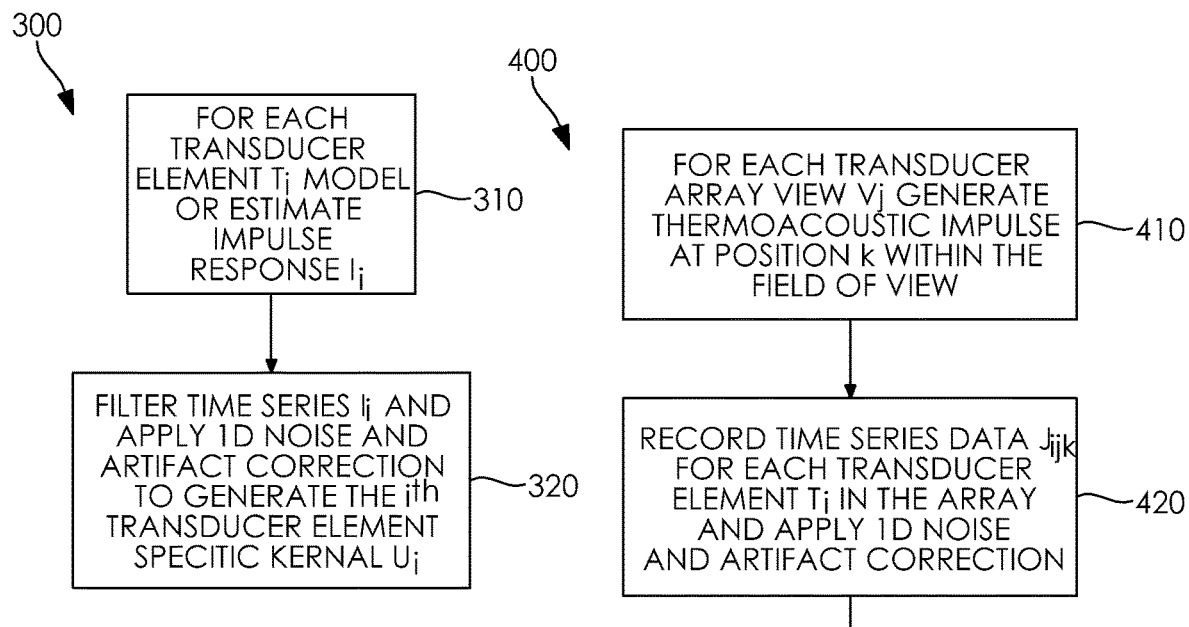
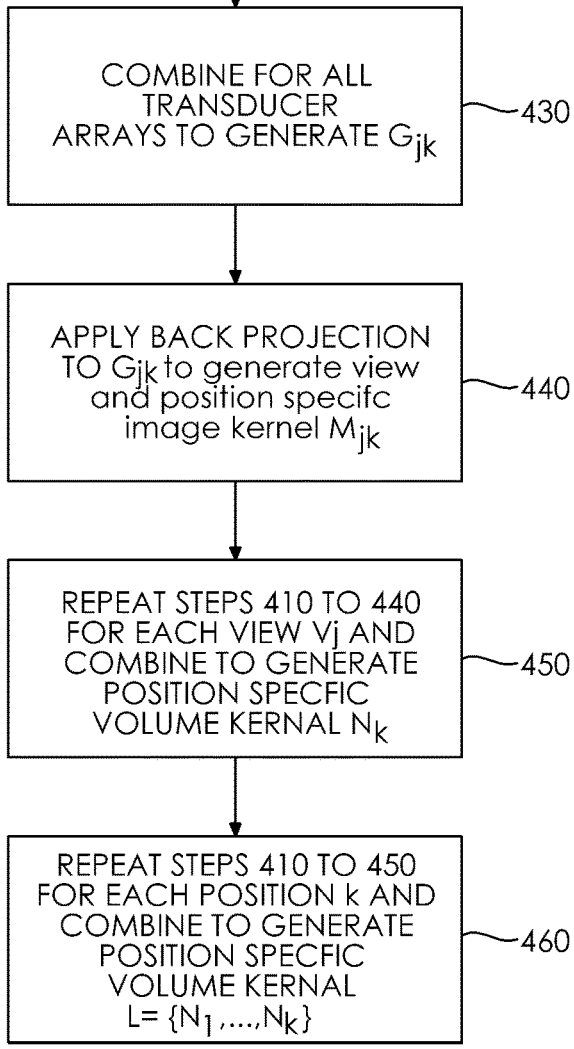
FIG. 3
FIG. 4

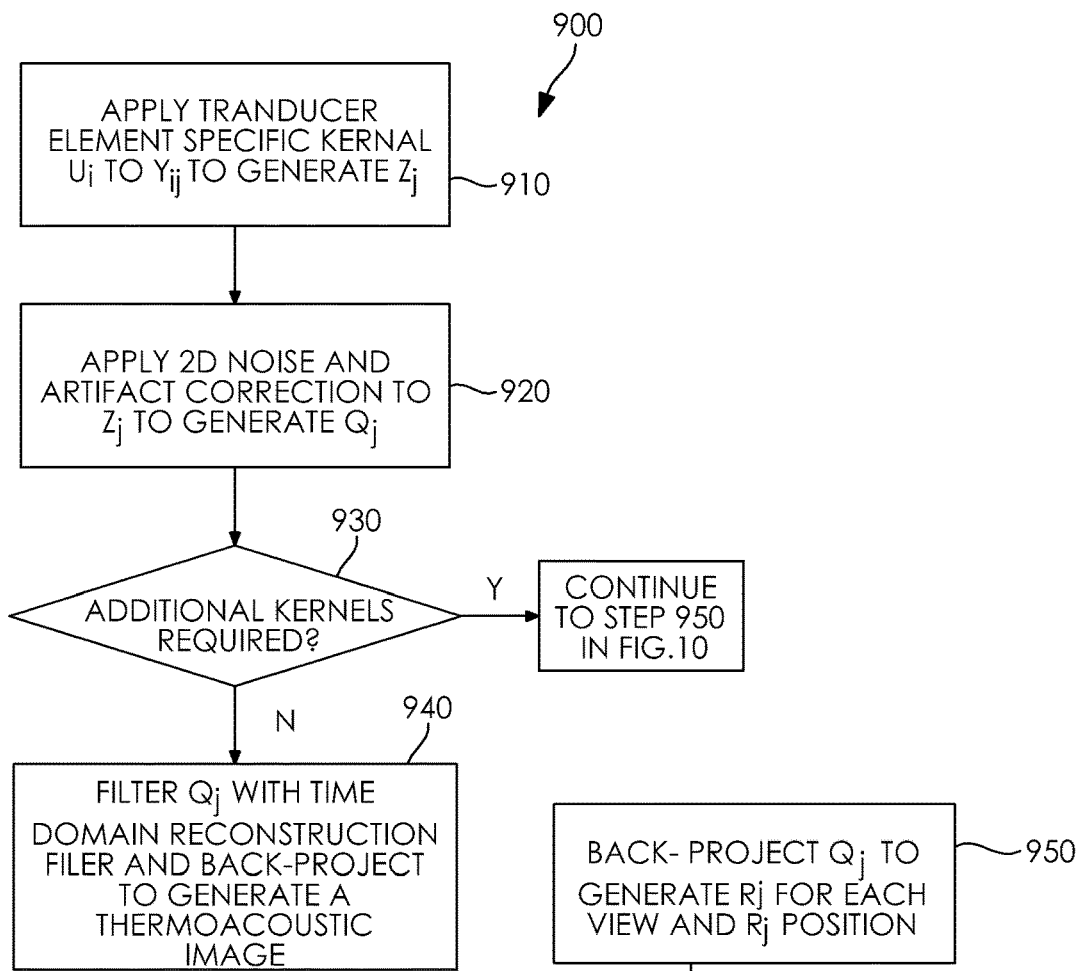

BEFORE (LEFT) AND AFTER (RIGHT) THE CORRECTION

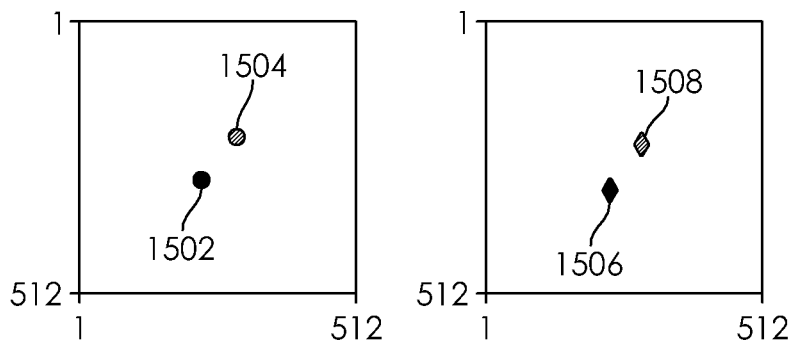
FIG. 15A  FIG. 15B
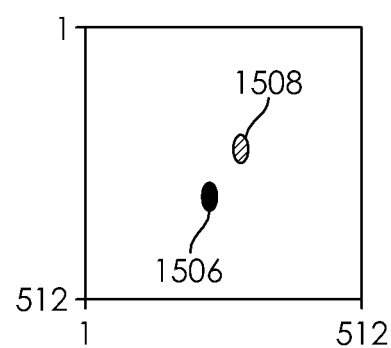
FIG. 15C

METHOD AND SYSTEM FOR RECONSTRUCTING A THERMOACOUSTIC IMAGE

FIELD

The subject disclosure relates to thermoacoustic imaging, and in particular to a method and system for reconstructing a thermoacoustic image.

BACKGROUND

Thermoacoustic imaging is an imaging modality that provides information relating to the thermoelastic properties of tissue. Thermoacoustic imaging uses short pulses of electromagnetic energy, such as radio frequency (RF) pulses, directed into a subject to heat an object (region) of interest within the subject rapidly, which causes the object to expand and then contract, resulting in acoustic pressure waves (signals) being induced in the subject that are detected using an acoustic receiver such as an ultrasound or thermoacoustic transducer array. The detected acoustic pressure waves are analyzed through signal processing, and processed for presentation and interpretation by an operator.

During signal processing of the acoustic pressure waves, sophisticated image reconstruction algorithms are employed that enable thermoacoustic images of the object to be generated by reconstructing heat absorption distribution within the object while reducing noise and other artifacts. Most thermoacoustic image reconstruction algorithms used to generate thermoacoustic images are derived from methods originally developed for other imaging modalities, such as conventional ultrasound and computed tomography (CT). As such, these image reconstruction algorithms are not optimized for processing thermoacoustic image data.

For example, conventional CT reconstruction algorithms are based on the projection-slice (or Fourier slice) theorem, which requires a large number of views or measurements around the object to be imaged. Given that x-rays and acoustic waves behave very differently as they propagate through tissue, conventional CT reconstruction algorithms are too simplistic at best.

Simply stated, each CT view of a given object constitutes a projection of the object along the plane of the transducer array. A Fourier transform of this projection corresponds to an infinitely-thin slice of the object, parallel to the plane. A full reconstruction of the object requires a dense sampling of the Fourier space, and hence a large number of CT views (or projections). In contrast, a single thermoacoustic view packs far more complex information than a simple projection of the object along the plane. Truncating the thermoacoustic view to a simple projection, followed by a dense sampling of views is highly inefficient.

In particular, one known image reconstruction algorithm involves deconvolving transducer array time-series data to obtain heat absorption projection data, filtering the projection data to reduce blurring effects using, for example, a Shepp-Logan or similar filter, and performing back-projections over all transducer elements of the transducer array to reconstruct the thermoacoustic image. One problem with this known image reconstruction algorithm however, is that time-domain filters, such as the Shepp-Logan filter, assume that the thermoacoustic data is complete i.e. that the thermoacoustic data comprises a large set of image views. As mentioned above, this assumption may not hold for thermoacoustic imaging, where a small number of views may be sufficient for reconstructing the thermoacoustic image. As such, applying filters such as the Shepp-Logan filter, may result in severe artifacts, thereby degrading the quality of the reconstructed thermoacoustic image.

As will be appreciated, improved techniques for reconstructing thermoacoustic images are desired. It is therefore an object at least to provide a novel method and system for reconstructing a thermoacoustic image.

SUMMARY

It should be appreciated that this Summary is provided to introduce a selection of concepts in a simplified form that are further described below in the Detailed Description. This Summary is not intended to be used to limit the scope of the claimed subject matter.

Accordingly, in one aspect there is provided a method for reconstructing a thermoacoustic image comprising: directing radio frequency (RF) energy pulses generated by an RF source into a tissue region of interest; detecting, at each of a plurality of views along a scanning trajectory of a transducer element array about the region of interest, acoustic signals generated within the region of interest in response to the RF energy pulses and generating thermoacoustic data; applying at least one correction kernel to the thermoacoustic data; and after the at least one correction kernel has been applied to the thermoacoustic data, reconstructing a thermoacoustic image therefrom.

In one or more embodiments, the at least one correction kernel is generated during a calibration procedure.

In one or more embodiments, the at least one correction kernel is a transducer element specific kernel to correct for different properties of individual transducer elements of the array. The transducer element specific kernel may be generated by: (i) estimating an impulse response of each transducer element of the array; (ii) applying a filter to the impulse responses based on one or more known unique characteristics of the transducer elements; and (iii) applying a noise and artifact correction to the filtered impulse responses. The one or more known unique characteristics may comprise at least one of center frequency, bandwidth and noise sensitivity.

In one or more embodiments, the at least one correction kernel is a view and position specific kernel to correct for differences in the relative relationship between the transducer element array and an object within the region of interest to be imaged at each view. The view and position specific kernel for a selected view may be generated by: (i) generating an acoustic impulse at a known impulse position within a field of view of the transducer element array; (ii) recording time-series thermoacoustic data for each transducer element of the transducer element array; (iii) combining the thermoacoustic data recorded for each transducer element to generate a matrix; and (iv) applying back projection to the matrix to generate the view and position specific kernel.

In one or more embodiments, the at least one kernel is a position specific volume kernel to correct for variations in spatial sensitivity as a result of transducer element array and scanning geometries. The position specific volume kernel may be generated by: (i) generating an acoustic impulse at a known impulse position within a field of view of the transducer element array; (ii) recording time-series thermoacoustic data for each transducer element of the transducer element array; (iii) combining the thermoacoustic data recorded for each transducer element to generate a matrix; (iv) applying back projection to the matrix to generate a view and position specific kernel; (v) repeating steps (i) to (iv) for each view of the transducer element array; and (vi) repeating steps (i) to (v) for each known impulse position within the field of view.

In one or more embodiments, multiple correction kernels may be applied to the thermoacoustic data. The correction kernels may comprise a transducer element specific kernel to correct for different properties of individual transducer elements of the array and a view and position specific kernel to correct for differences in the relative relationship between the transducer element array and an object within the region of interest to be imaged at each view. The correction kernels may comprise a transducer element specific kernel to correct for different properties of individual transducer elements of the array and a position specific volume kernel to correct for variations in spatial sensitivity as a result of transducer element array and scanning geometries.

In one or more embodiments, the scanning trajectory is circular or non-circular.

In one or more embodiments, the method may further comprise applying a noise and artifact correction algorithm to the thermoacoustic data prior to reconstructing the thermoacoustic image.

According to another aspect there is provided a thermoacoustic imaging system comprising: a radio frequency source configured to emit RF pulses into a region of interest and heat tissue therein; a transducer element array moveable along a scanning trajectory about the region of interest and configured to receive acoustic signals generated in response to heating of the tissue, at each of a plurality of views along the scanning trajectory, and generate thermoacoustic data; and one or more processors configured to: apply at least one kernel to the thermoacoustic data based on at least one of (i) characteristics of transducer elements of the at least one transducer array, (ii) differences in the relative relationship between the transducer element array and an object in the region of interest to be imaged at each view, and (iii) variations in spatial sensitivity as a result of transducer element array and scanning geometries; and reconstruct a thermoacoustic image after the at least one kernel has been applied to the thermoacoustic data.

According to another aspect there is provided a method of calibrating a thermoacoustic imaging system comprising a transducer element array that includes a plurality of transducer elements and that is moved along a scanning trajectory about a region of interest during thermoacoustic imaging to detect acoustic signals induced within the region of interest at a plurality of views along the scanning trajectory, the method comprising: generating at least one of a transducer element specific kernel, a view and position specific kernel and a position specific volume kernel, the transducer element specific kernel configured to correct for different properties of individual transducer elements of the array, the view and position specific kernel configured to correct for differences in the relative relationship between the transducer element array and an object within the region of interest to be imaged at each view, and the position specific volume kernel configured to correct for variations in spatial sensitivity as a result of transducer element array and scanning geometries; and storing the at least one kernel in memory for use by one or more processors during thermoacoustic image reconstruction.

BRIEF DESCRIPTION OF THE DRAWINGS

Embodiments will now be described more fully with reference to the accompanying drawings in which:

FIG. 3 is a flowchart outlining a method of generating a transducer element specific kernel;

FIG. 4 is a flowchart outlining a method of generating a view and position specific image kernel and a position specific volume kernel;

FIGS. 9 to 11 are flowcharts outlining a method of applying one or more kernels to thermoacoustic data;

FIG. 15A shows a pair of true objects within a region of interest to be imaged;

FIG. 15B shows a conventionally reconstructed image of the objects of FIG. 15A at a single view; and FIG. 15C shows a thermoacoustic image reconstructed of the objects of FIG. 15A at a single view using the method of FIG. 2.

DETAILED DESCRIPTION OF THE EMBODIMENTS

Figure 1:
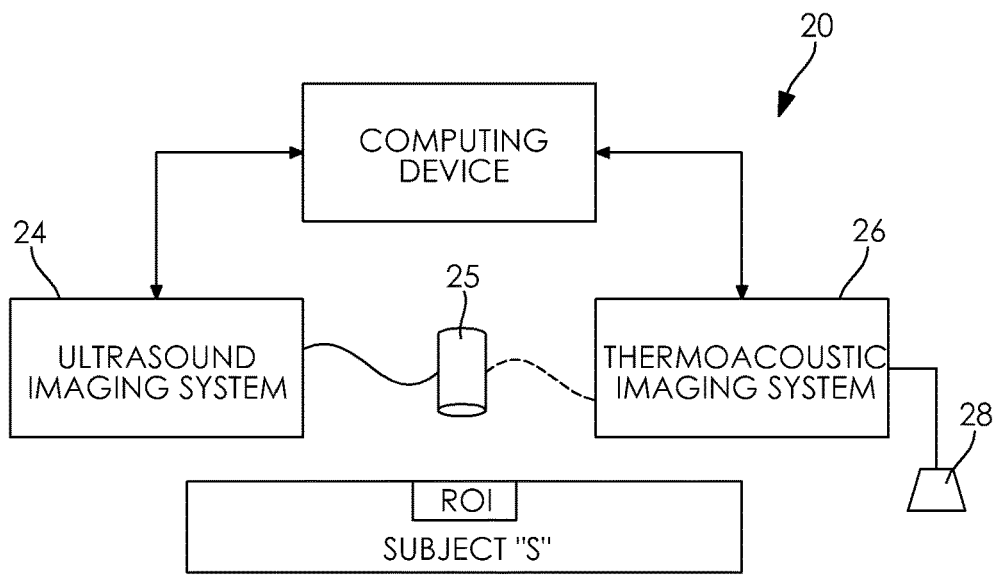
FIG. 1 is a schematic view of an imaging system.

The foregoing summary, as well as the following detailed description of certain examples will be better understood when read in conjunction with the appended drawings. As used herein, an element or feature introduced in the singular and preceded by the word "a" or "an" should be understood as not necessarily excluding the plural of the elements or features. Further, references to "one example" or "one embodiment" are not intended to be interpreted as excluding the existence of additional examples or embodiments that also incorporate the described elements or features. Moreover, unless explicitly stated to the contrary, examples or embodiments "comprising" or "having" or "including" an element or feature or a plurality of elements or features having a particular property may include additional elements or features not having that property. Also, it will be appreciated that the terms "comprises", "has", "includes" means "including but not limited to" and the terms "comprising", "having" and "including" have equivalent meanings.

As used herein, the term "and/or" can include any and all combinations of one or more of the associated listed elements or features.

It will be understood that when an element or feature is referred to as being "on", "attached" to, "connected" to, "coupled" with, "contacting", etc. another element or feature, that element or feature can be directly on, attached to, connected to, coupled with or contacting the other element or feature or intervening elements may also be present. In contrast, when an element or feature is referred to as being, for example, "directly on", "directly attached" to, "directly connected" to, "directly coupled" with or "directly contacting" another element of feature, there are no intervening elements or features present.

It will be understood that spatially relative terms, such as "under", "below", "lower", "over", "above", "upper", "front", "back" and the like, may be used herein for ease of description to describe the relationship of an element or feature to another element or feature as illustrated in the FIG.s. The spatially relative terms can however, encompass different orientations in use or operation in addition to the orientations depicted in the FIG.s.

In the following, a method and system for reconstructing a thermoacoustic image are described. In one form, the method comprises: directing radio frequency (RF) energy pulses generated by an RF source into a tissue region of interest; detecting, at each of a plurality of views along a scanning trajectory of a transducer element array about the region of interest, acoustic signals generated within the region of interest in response to the RF energy pulses and generating thermoacoustic data; applying at least one correction kernel to the thermoacoustic data; and after the at least one kernel has been applied to the thermoacoustic data, reconstructing a thermoacoustic image therefrom.

Before describing the subject method and system for reconstructing a thermoacoustic image, it is worthwhile to provide further background concerning thermoacoustic image reconstruction and the state of the art. Developing accurate and robust image reconstruction methods is one of the key challenges encountered in thermoacoustic imaging. Various image reconstruction algorithms have been developed for thermoacoustic imaging. For example, using the spherical Radon transformation on thermoacoustic image data has made tomography reconstruction algorithms applicable to thermoacoustic image reconstruction. Exact inverse solutions have been found for different scanning geometries in both the frequency domain and the time domain. Approximate reconstruction algorithms, such as time-domain delay-and-sum (DAS) beamforming method and the optimal statistical approach, have also been proposed for thermoacoustic image reconstruction. However, a common assumption of these reconstruction algorithms is that the surrounding tissue is acoustically homogeneous. Unfortunately, this assumption is inadequate in many medical imaging applications. According to previous studies, the sound speed in a human female breast varies widely from 1430 m/s to 1570 m/s around the commonly assumed sound speed of 1540 m/s. The heterogeneous acoustic properties of biological tissues cause amplitude and phase distortions in the acoustic signals, which can result in significant degradation in imaging quality.

In ultrasound tomography (UT), wavefront distortion due to heterogeneity of biological tissue has been studied extensively. Various wavefront correction methods have been proposed. However, they are not highly effective at correcting severe amplitude distortions, and they usually involve complicated procedures. The problem in thermoacoustic imaging is somewhat different from that in UT. In breast UT, the amplitude distortion caused by refraction is more problematic than the phase distortion induced by acoustic speed variation. In thermoacoustic imaging, however, even for the biological tissue, such as the breast tissue, with a relatively weak heterogeneity, phase distortion dominates amplitude distortion.

X-ray mammography is a clinical tool for breast cancer screening. Although effective, it has difficulties in imaging premenopausal breasts, and has the medical and environmental disadvantages attendant upon the use of ionizing radiation.

Purely-microwave imaging of biological tissues is fundamentally limited to poor resolution (on the order of 10 mm) because of the larger wavelength of microwave. Also, purely-microwave imaging has difficulties in multi-channel detection of microwave without cross coupling, in reconstruction algorithms, and especially in achieving good spatial resolution because of the strong diffraction of microwaves. Purely-ultrasound imaging (ultrasonography), an established medical imaging modality, can yield good spatial resolution, but has poor contrast for early-stage tumors. Electromagnetically-induced thermoacoustic imaging, and microwave-induced or radio frequency induced thermoacoustic imaging in particular, can potentially bridge the gap and fuse the advantages of the two imaging modalities. The contrast between tumors and normal tissues in the electromagnetic wave regime is very good. Cancerous breast tissues, for example, are found to be 2-5 times more strongly absorbing than surrounding normal breast tissues in the electromagnetic wave range, which has been attributed to an increase in bound water and sodium within malignant cells.

Turning now to FIG. 1, an exemplary imaging system is shown and is generally identified by reference numeral 20. As can be seen, in this embodiment the imaging system 20 comprises a programmed computing device 22 communicatively coupled to an ultrasound imaging system 24 and to a thermoacoustic imaging system 26. The ultrasound imaging system 24 and thermoacoustic imaging system 26 are configured to obtain ultrasound image data and thermoacoustic image data, respectively, of a region of interest ROI associated with a subject S. The region of interest ROI encompasses structure e.g. tissue, an internal organ or other feature, etc. to be imaged (hereinafter referred to as "object").

The programmed computing device 22 in this embodiment is a personal computer, server or other suitable processing device comprising, for example, a processing unit comprising one or more processors, system memory (volatile and/or non-volatile memory), other non-removable or removable memory (e.g., a hard disk drive, RAM, ROM, EEPROM, CD-ROM, DVD, flash memory, etc.) and a system bus coupling the various computer components to the processing unit. The computing device 22 may also comprise networking capabilities using Ethernet, Wi-Fi, and/or other suitable network format, to enable connection to shared or remote drives, one or more networked computers, or other networked devices. One or more input devices, such as a mouse and a keyboard (not shown) are coupled to the computing device 22 for receiving operator input. A display device (not shown), such as one or more computer screens or monitors, is coupled to the computing device 22 for displaying one or more generated images that are based on ultrasound image data received from the ultrasound imaging system 24 and/or the thermoacoustic image data received from thermoacoustic imaging system 26.

The ultrasound imaging system 24 comprises an acoustic receiver in the form of an ultrasound transducer 25 that is disconnectable from the ultrasound imaging system 24. The ultrasound transducer 25 in this embodiment comprises a single linear array of transducer elements $T_i$. In particular, the linear transducer element array comprises a line or string of one hundred and twenty eight (128) transducer elements $T_i$. Those of skill in the art will however appreciate that the transducer element array may have alternative configurations. For example, the linear array of transducer elements may comprise fewer or more than 128 transducer elements $T_i$. The transducer element array may also be curved such as in an arc. Alternatively, the transducer element array may be two-dimensional and comprise multiple rows and columns of transducer elements. The two-dimensional array of transducer elements may be planar or curved.

Ultrasound transducer 25 is configured to emit sound waves into the region of interest ROI of the subject S. The sound waves directed into the region of interest ROI of the subject S echo off structure within the region of interest ROI, with different structure reflecting varying degrees of sound. Echoes that are received by the ultrasound transducer 25 are processed by the ultrasound imaging system 24 before being communicated as ultrasound image data to the computing device 22 for further processing and for presentation and interpretation by an operator. In this embodiment, the ultrasound imaging system 24 utilizes B-mode ultrasound imaging techniques assuming a nominal speed of sound of 1,540 m/s. As ultrasound imaging systems are known in the art, further specifics of the ultrasound imaging system 24 will not be described further herein.

The thermoacoustic imaging system 26 comprises a radio-frequency (RF) source 28 that is configured to emit short pulses of RF energy that are directed into the region of interest ROI of the subject S. In this embodiment, the RF source 28 has a frequency between about 10 Mhz and 100 GHz and has a pulse duration between about 0.1 nanoseconds and 10 nanoseconds. The RF energy pulses delivered to the region of interest ROI heat the structure therein thereby to induce acoustic signals within the structure. In order to detect the acoustic signals, the thermoacoustic imaging system 26 makes use of the ultrasound transducer 25 by disconnecting it from the ultrasound imaging system 24 and connecting it to the thermoacoustic imaging system 26 as designated by the dashed line. Acoustic signals detected by the transducer 25 are processed and communicated as thermoacoustic image data to the computing device 22 for further processing and for presentation as thermoacoustic images that can be interpreted by the operator. As will be appreciated, as both the ultrasound imaging system 24 and the thermoacoustic imaging system 26 make use of the transducer 25, coordinate mapping between different acoustic receivers (transducer element arrays) is not required thereby simplifying ultrasound and thermoacoustic image registration.

Figure 2:
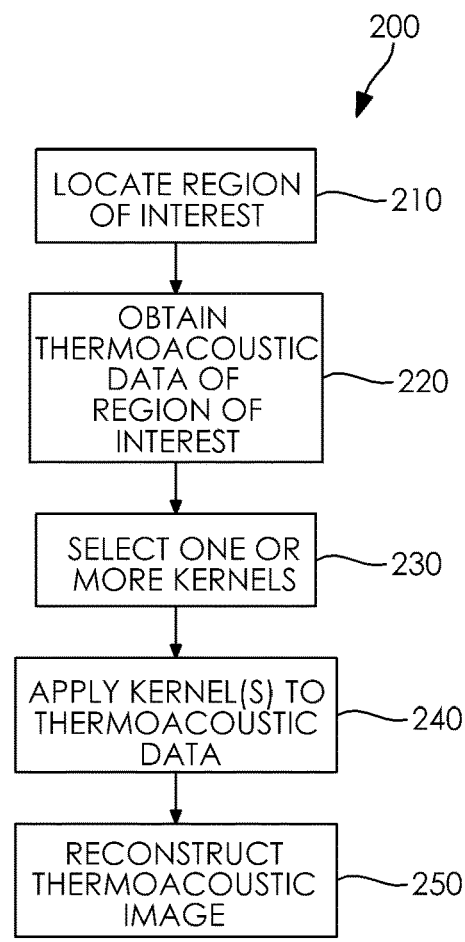
FIG. 2 is a flowchart outlining a method of reconstructing a thermoacoustic image.

Turning now to FIG. 2, a thermoacoustic imaging procedure is generally shown and referred to by reference numeral 200. Initially during the thermoacoustic imaging procedure 200, the region of interest ROI of the subject S encompassing the object to be imaged is located (step 210). In this embodiment, the region of interest ROI is located using the ultrasound imaging system 24 by moving the ultrasound transducer 25 over the subject S. Ultrasound image data obtained by the ultrasound transducer 25 of the ultrasound imaging system 24 is communicated to the computing device 22. The ultrasound image data is processed by the computing device 22 and a reconstructed ultrasound image is presented on the display device. This allows the operator to move the ultrasound transducer array 25 on the subject's body until the region of interest ROI is located.

Once the region of interest ROI has been located, thermoacoustic imaging of the region of interest can be carried out. At this stage, the ultrasound transducer 25 is disconnected from the ultrasound imaging system 24 and is connected to the thermoacoustic imaging system 26. During thermoacoustic imaging, the transducer 25, which now functions as a thermoacoustic transducer, is moved along a scanning trajectory relative to the region of interest ROI. The scanning trajectory may be circular or non-circular, such as a spiral. The configuration of the scanning trajectory is typically dependent on the portion of the subject S being scanned. For example, if a breast of the subject S is being scanned, the scanning trajectory will typically be in the form of a spiral as the transducer 25 is moved around the breast from the nipple towards the subject's body or vice versa. At various positions j of the transducer 25 along the scanning trajectory, the RF source 28 is conditioned to emit short pulses of RF energy that are directed into the subject S to heat the object within the region of interest ROI rapidly, which causes the object to expand and then contract, resulting in acoustic signals being induced in the subject S. In response, the acoustic signals are detected by the transducer elements $T_i$ of the array resulting in thermoacoustic data being captured and conveyed to the computing device 22 (step 220). Each position j of the transducer element array along the scanning trajectory where thermoacoustic data is captured is referred to as a view $V_j$. As will be appreciated, depending on the scanning trajectory, at each view $V_j$, the relative relationship between the transducer element array of the transducer 25 and the object may be different. Thus, thermoacoustic data are captured by the transducer elements of the array at each view $V_j$ and the captured thermoacoustic data are then signal processed by the computing device 22 and a reconstructed thermoacoustic image is generated and presented to the operator (step 250).

Prior to reconstructing the thermoacoustic image at step 250, the captured thermoacoustic data may be subject to kernels to correct for (i) different properties of individual transducer elements $T_i$ of the array, and/or (ii) variations in spatial sensitivity as a result of differences in the relative relationship between the transducer element array and the object at each view, and/or the transducer element array and scanning trajectory geometries. Depending on the corrections to the thermoacoustic data that are required, prior to thermoacoustic image reconstruction at step 250, one or more of the kernels are selected (step 230) and the selected kernel(s) is(are) applied to the thermoacoustic data (step 240). The above kernels are determined during calibration of the imaging system 20 as will now be described.

As will be appreciated, due to imperfections in manufacturing processes, each transducer element $T_i$ of the array may have unique properties or characteristics. For example, although the center frequencies of the transducer elements $T_i$ will likely be very similar, bandwidths and noise sensitivities of the transducer elements $T_i$ may vary. As such, thermoacoustic image data obtained by one transducer element $T_i$ of the array may be different than thermoacoustic image data obtained by another transducer element of the array. The kernel that corrects for the different properties of individual transducer elements $T_i$ of the array is referred to as the transducer element specific kernel $U_i$. Those of skill in the art will appreciate that in some embodiments, the transducer elements of the array may be arranged in groups based on center frequency. For example, in the case of the 128 transducer elements $T_i$ in the array, 64 of the transducer elements $T_i$ may have a center frequency centered around 5 MHz and 64 of the transducer elements $T_i$ may have a center frequency centered around 2 MHz.

The transducer element specific kernel $U_i$ is defined for the transducer elements $T_i$ of the array according to method 300 shown in FIG. 3. During the method, for each transducer element $T_i$ in the array, the impulse response $I_i$ of the transducer element $T_i$ is estimated or modeled (step 310). The impulse responses $I_i$ of the transducer elements $T_i$ are then filtered based on prior knowledge (i.e. the known one or more characteristics of the transducer elements $T_i$) and a 1D noise and artifact reduction is applied to the filtered impulse responses $I_i$ using a bandpass filter or the like. The filtered impulse responses for the transducer elements $T_i$ are then used to generate the transducer element specific kernel $U_i$ (step 320).

As mentioned above, for some scanning trajectories, the relative relationship between the transducer element array and the object within the region of interest ROI at the various views there along may differ. For example, in the case of a spiral scanning trajectory to scan a breast, the view near the apex of the spiral will be different than the view at the wider end of the spiral. Also depending on the layout of the transducer elements $T_i$ of the array and how the transducer element array is moved during the scan, the transducer 25 may not have uniform spatial sensitivity within its field of view at the various views. The kernels that correct for variations in spatial sensitivity are referred to as the view and position specific image kernel $M_{jk}$ and the position specific volume kernel L.

Figure 5:
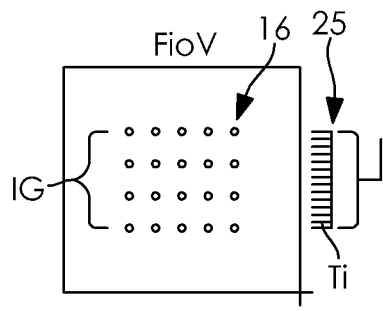
FIG. 5 shows an impulse grid, impulse positions within the impulse grid and a transducer forming part of the imaging system.

The view and position specific image kernel $M_{jk}$ and the position specific volume kernel L are determined according to method 400 shown in FIG. 4. Initially, an impulse grid IG substantially corresponding in size to the field of view FOV of the transducer element array and comprising a rectangular array of impulse positions k is provided (see FIG. 5). The impulse grid IG is configured to generate an acoustic impulse at each impulse position k in response to RF pulses directed towards the impulse grid using the RF source 28. In this embodiment, the impulse grid IG is defined by an array of metal wires or balls. Alternatively, the acoustic impulses may be simulated.

A view $V_j$ of the transducer element array along the scanning trajectory is then selected and the transducer element array is positioned at the selected view $V_j$. The impulse grid IG is then conditioned to generate an acoustic impulse at a selected impulse position k (step 410). At the selected view and in response to the generated acoustic impulse, each transducer element $T_i$ generates time-series thermoacoustic data $J_{ijk}$, which is recorded by the computing device 22 and a 1D noise and artifact reduction is then applied to the time-series thermoacoustic data $J_{ijk}$ (step 420). The time-series thermoacoustic data $J_{ijk}$ generated by the transducer elements $T_i$ of the array is combined to form matrix $G_{jk}$ (step 430). A back-projection is then applied to the matrix $G_{jk}$ to yield a view and position specific image kernel $M_{jk}$ for the selected view and impulse position (step 440).

Steps 410 to 440 are then repeated for each view $V_j$ of the transducer element array along the scanning trajectory. As a result, view and position specific image kernels $M_{jk}$ for each view are generated at each impulse response position. The generated view and position specific image kernels $M_{jk}$ are then combined to generate a position specific volume kernel $N_k$ (step 450).

Steps 410 to 450 are then repeated for acoustic impulses generated at each of the other impulse positions k of the impulse grid IG. As a result, position specific volume kernels $N_k$ for each impulse position k are generated. The generated position specific volume kernels $N_k$ are then combined to generate the position specific volume kernel $L=\{N_1, \ldots, N_k\}$ (step 460).

Figure 6:
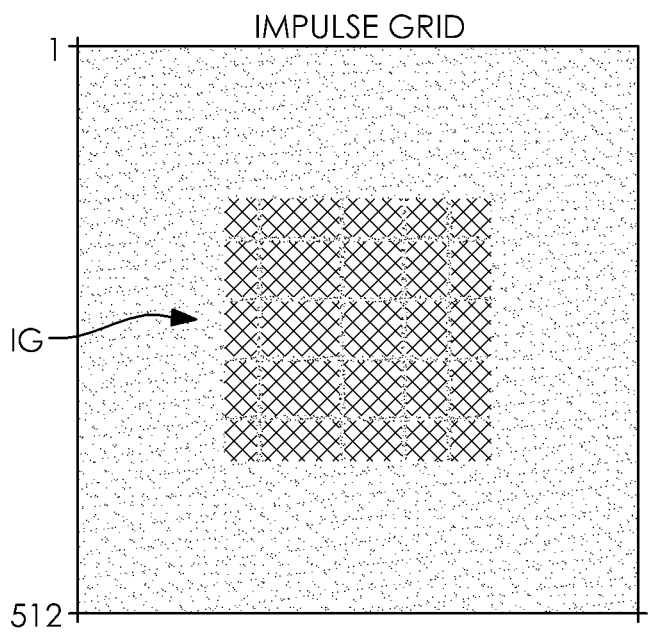
FIG. 6 shows image artifacts, impulse positions within the impulse grid and a transducer forming part of the imaging system.

Referring back to FIG. 5, the transducer 25 together with the array of transducer elements $T_i$ is shown to one side of the impulse grid IG within the field of view FOV of the transducer. Acoustic impulses are generated at each impulse location k of the impulse grid IG and are detected by the transducer elements $T_i$. FIG. 6 is a view similar to FIG. 5 and shows artifacts 600 that modify acoustic impulses generated by the impulse grid IG.

Figure 7:
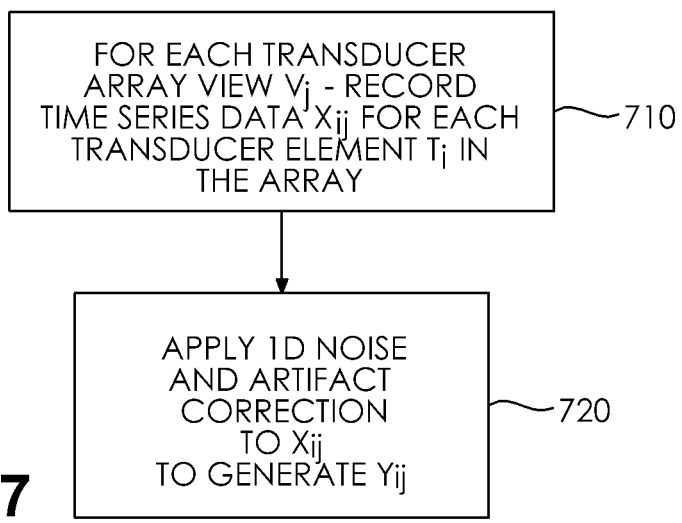
FIG. 7 is a flowchart outlining a method of obtaining thermoacoustic data.

As mentioned previously, during the thermoacoustic imaging procedure 200, at step 220, for each view $V_j$ along the scanning trajectory thermoacoustic data are captured by directing RF pulses into the region of interest ROI using the RF source 28, detecting the resultant acoustic signals generated within the region of interest, recording the time-series thermoacoustic image data $X_{ij}$ generated by each transducer element $T_i$ in the array in response to the acoustic signals (see step 710 in FIG. 7) and applying 1D noise and artifact correction to yield thermoacoustic data $Y_{ij}$ (step 720). Each transducer element $T_i$ of the array is sensitive to acoustic signals from a broad range of angles and time-delays. As a result, for 2D images, rather than the thermoacoustic data for each view corresponding to a thin slice of the object's Fourier transform, the thermoacoustic data for the view instead corresponds to a broad fan or bow-tie of spatial frequencies in the 2D transform space. For 3D images, the thermoacoustic data for the view corresponds to a double-napped cone. In order to obtain an accurate reconstruction of the object within the region of interest ROI, the number of views $V_j$ along the scanning trajectory is selected so that, in the case of 2D images, the bow-ties for the views overlap and completely fill the Fourier transform space, and in the case of 3D images, the double-napped cones overlap and completely fill the Fourier transform space.

At steps 230 and 240, one or more of the kernels generated during calibration is selected and applied to the thermoacoustic data $Y_{ij}$. In this embodiment, the one or more kernels are selected at step 230 according to method 800 shown in FIG. 8. If all of the thermoacoustic data was obtained at the same view $V_j$ (step 810), the transducer element specific kernel $U_i$ is selected (step 820). If the thermoacoustic data was obtained at different views $V_j$ and each view has distinct characteristics than the other views (step 830), the transducer element specific kernel $U_i$ and the view and position specific image kernels $M_{jk}$ are selected (step 840). If the thermoacoustic data was obtained at different views $V_j$ and all of the views are equivalent but the thermoacoustic data obtained at each position k within the field of view has distinct characteristics (step 850), the transducer element specific kernel $U_i$ and the position specific volume kernel L are selected (step 860).

Once the kernels have been selected at step 230, the kernels are applied to the thermoacoustic data $Y_{ij}$ (step 240). In this embodiment, the kernels are applied according to method 900 shown in FIGS. 9 to 11 as will be described.

Figure 8:
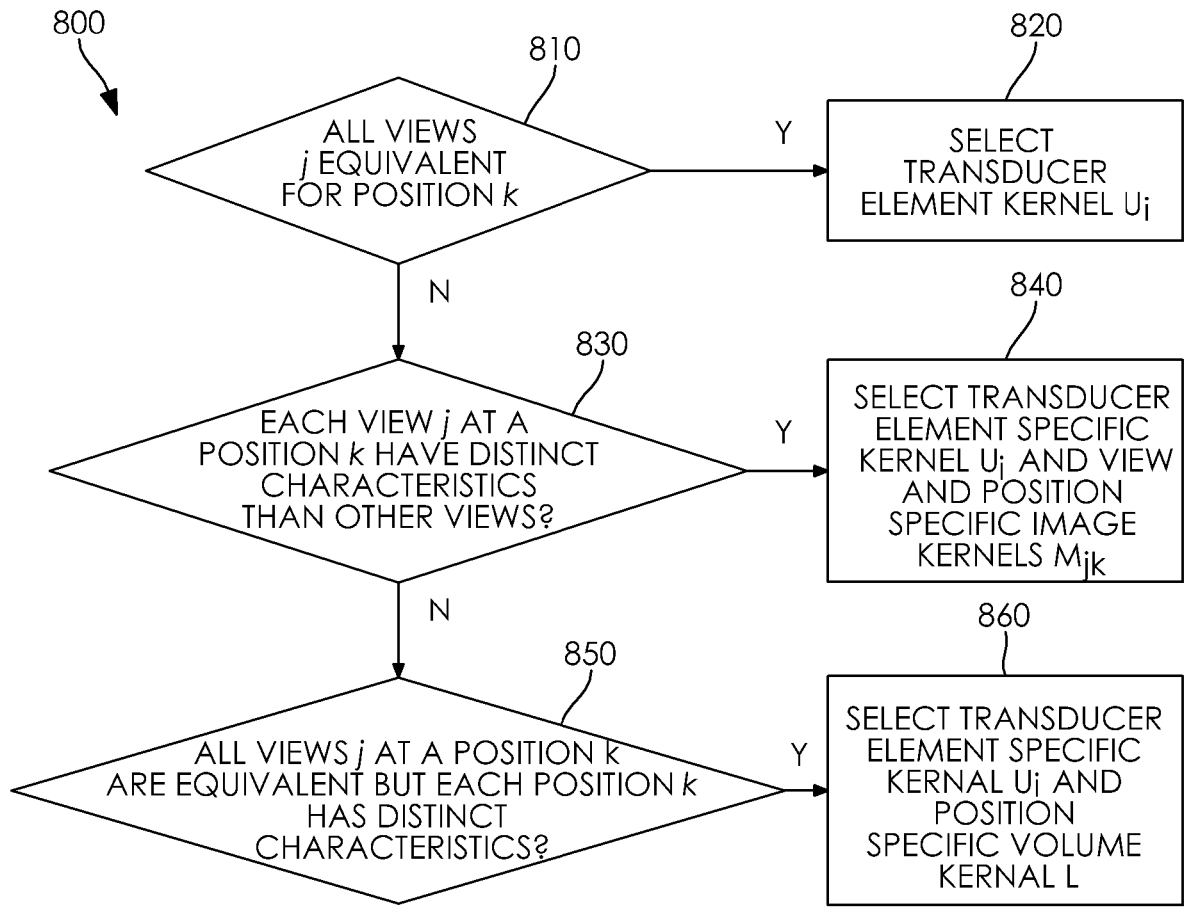
FIG. 8 is a flowchart outlining a method of selecting one or more kernels.

As will be appreciated, as shown FIG. 8 at each of steps 820, 840 and 860, the transducer specific kernel $U_i$ is selected. As a result, following step 720, for each view, the transducer element specific kernel is applied to the thermoacoustic data $Y_{ij}$ by deconvolving the transducer element specific kernel $U_i$ from thermoacoustic data $Y_{ij}$ to yield resultant matrix $Z_j$ (step 910). A 2D noise and artifact correction is applied to each matrix $Z_j$ to generate resultant matrices $Q_j$ (step 920). A check is performed to determine if additional kernels need to be applied (step 930). If the transducer element specific kernel $U_i$ is the only kernel to be applied, the matrices $Q_j$ are filtered with a time domain reconstruction filter and are back-projected to reconstruct a thermoacoustic image of the object within the region of interest (step 940).

If, at step 930, the transducer element specific kernel $U_i$ is not the only kernel to be applied, the method continues to step 950 in FIG. 10. During step 950, for each view $V_j$, matrix $Q_j$ is back-projected to generate matrix $R_j$. A check is then performed to determine which kernel is to be applied (step 960). If the view and position specific image kernel $M_{jk}$ is to be applied, the view and position specific image kernel $M_{jk}$ is applied to each matrix $Q_j$ to generate a resultant matrix $O_{jk}$. The resultant matrices $O_{jk}$ for the views are combined to generate a matrix $E_k$ (step 980) and the method continues to step 250 of method 200. As will be appreciated, matrix $E_k$ is sufficient to allow an image of the object within the region of interest ROI to be reconstructed.

Figure 11:
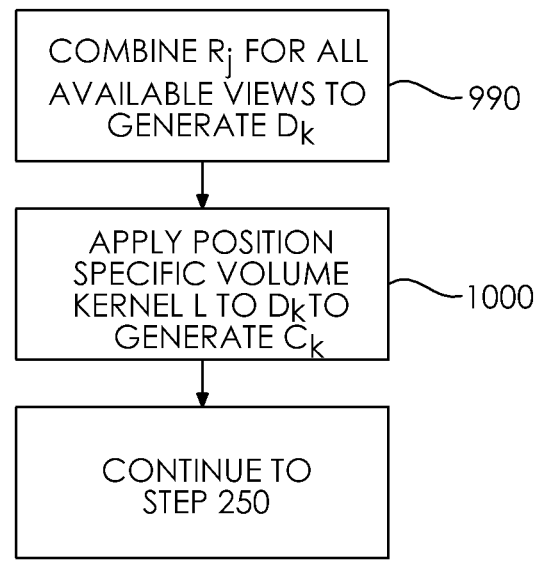

If, at step 960, the position specific volume kernel L is to be applied, the method continues to step 990 in FIG. 11. During step 990, the matrices $R_j$ generated for all of the views are combined to generate matrix $D_k$. The position specific volume kernel L is applied to matrix $D_k$ to generate a matrix $C_k$ (step 1000) and the method continues to step 250 of method 200. As will be appreciated, matrix $C_k$ is sufficient to allow an image of the object within the region of interest ROI to be reconstructed.

During step 250 of method 200, a thermoacoustic image of the object within the region of interest ROI is reconstructed by spatially combining the images of matrix $E_k$ or $C_k$. As will be appreciated, the spatial combination of images is a weighted combination where the weights are determined by factors such as corresponding impulse locations, amount of overlap between images, etc. (see FIG. 13).

Figure 12A:
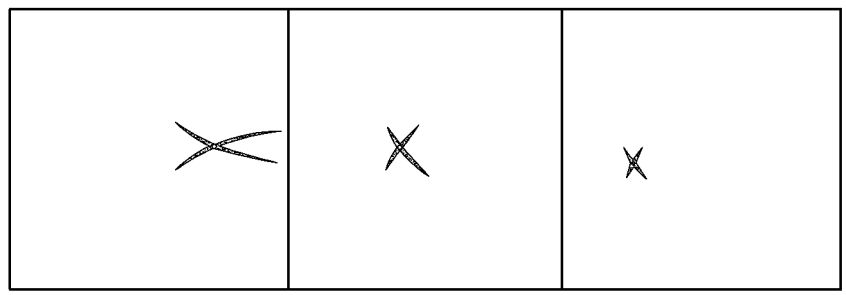
FIG. 12A shows impulse responses from impulse positions in a field of view of the transducer in the image domain.

FIG. 12A shows impulses 1202, 1204 and 1206 are at different positions k within the field of view of the transducer 25 at a single view. FIG. 12A is shown in the image domain. The impulse responses are filtered and back-projected.

Figure 12B:
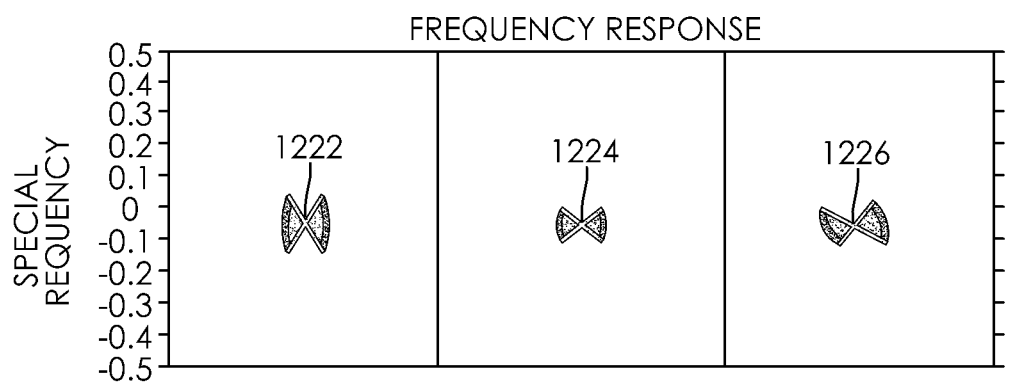
FIG. 12B shows impulse responses from impulse positions in the field of view of the transducer in the frequency domain.

FIG. 12B shows impulses 1222, 1224, 1226 from a single view with two-dimensional frequency responses corresponding to positions k of the impulses 1202, 1204, 1206 of FIG. 12A, respectively. FIG. 12B is shown in the frequency domain. The impulses responses are also filtered and back-projected. Each impulse 1202, 1204 and 1206 appears unique at each position. The view and position specific image kernel $M_{jk}$ is required to correct for this spatial variability.

Figure 13:
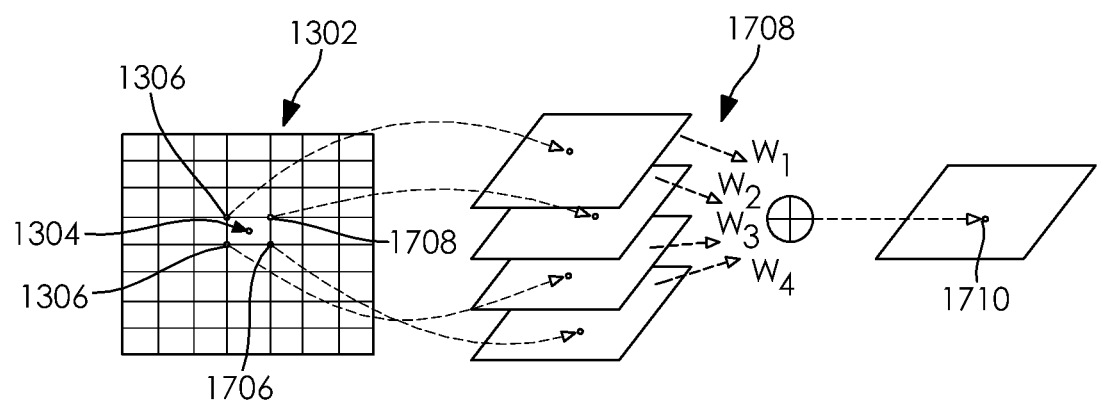
FIG. 13 shows a spatial combination process to generate a thermoacoustic image.

FIG. 13 shows an example of a spatial combination method used to generate a the reconstructed thermoacoustic image. Shown are reconstruction grid 1302, image 1304, impulse locations 1306, filtered images 1308, and diffraction corrected image 1310.

Figure 14:
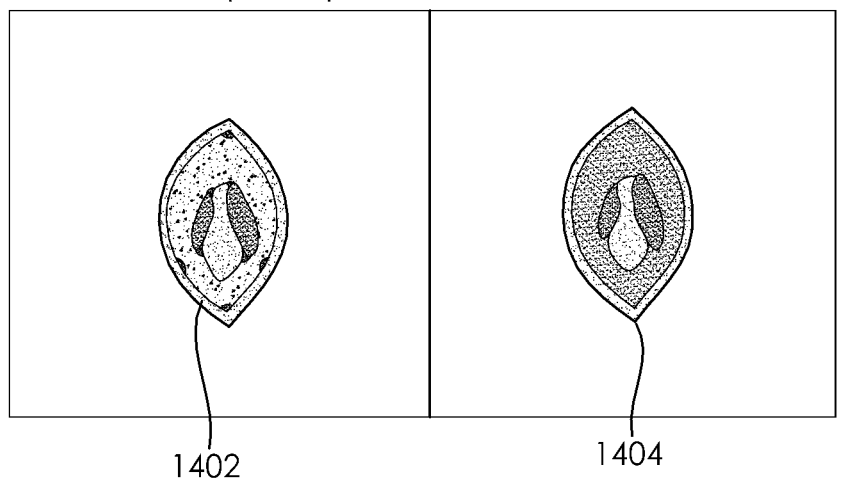
FIG. 14 shows a thermoacoustic image reconstructed using conventional methods and a thermoacoustic image reconstructed using the method of FIG. 2.

FIG. 14 compares conventional image reconstruction to the subject reconstruction method. The images are shown at a single view. The object in the conventional image reconstruction is identified by numeral 1402 and the object in the image reconstructed using the subject method is identified by numeral 1404.

FIG. 15A shows true objects 1502 and 1504 in a region of interest.

FIG. 15B shows the objects 1506, 1508 in a conventionally reconstructed image.

FIG. 15C shows the objects 1510, 1512 in an image reconstructed in accordance with the subject method.

Although in embodiments described above, the ultrasound imaging system 24 and thermoacoustic imaging system 26 make use of the same transducer 25, those of skill in the art will appreciate that the thermoacoustic imaging system 26 may have its own acoustic receiver in the form of a thermoacoustic transducer having an array of transducer elements. In this case, the ultrasound transducer 25 and the thermoacoustic transducer may be mechanically interconnected so that the spatial relationship between the transducer element array of the ultrasound transducer, the transducer element array of the thermoacoustic transducer and the RF source 28 are known. The spatial relationship is set using a centerline of the ultrasound transducer element array, the thermoacoustic transducer element array, and RF source 28. Each centerline is defined as being a mid-point of an area of the respective transduce array.

In this embodiment, the spatial relationship between the ultrasound transducer element array and the thermoacoustic transducer element arrays is such that the centerline of the thermoacoustic transducer element array is set at know angle $\alpha$ with respect to the centerline (also known as the axial axis or ultrasound transducer element array beam axis) of the ultrasound transducer element array. The spatial relationship between the thermoacoustic transducer element array and the RF source 28 is such that the centerline of the RF source 28 is spaced-apart and generally parallel to the centerline of the thermoacoustic transducer element array.

The imaging system 20 utilizes the known spatial relationship between the ultrasound transducer element array 30 and the thermoacoustic transducer element array to increase the precision and accuracy of thermoacoustic image and ultrasound image registration.

Although in embodiments described above, the impulse response of each transducer element is estimated or modeled, those skilled in the art will appreciate that in another embodiment, the impulse response of each transducer element may be acquired using acoustic impulses either generated by the impulse grid or simulated.

Other aspects of the method and system according to the subject disclosure are exemplified in the following clauses:

A1. A method of thermoacoustic tomography image reconstruction that utilizes a thermoacoustic imaging system, the method comprising:
  recording time-series data for each respective transducer in the thermoacoustic imaging system;
  deconvolving transducer element specific kernels for each respective transducer in the thermoacoustic imaging system;
  filtering with a time domain reconstruction filter and then back-projecting to generate at least one back-projected image; and
  spatially combining the least one back-projected image to generate a reconstructed image.

A2. The method of clause A1, further comprising denoising and correcting with algorithms to generate corrected time-series data for each transducer, immediately after the recording step.

A3. The method of clause A2, further comprising applying 2-D denoising and artifact correction algorithms to generate corrected deconvolved time-series data, immediately after the deconvolving step.

A4. The method of clause A1, further comprising applying a 2-D denoising and artifact correction algorithms to generate corrected deconvolved time-series data, immediately after the deconvolving step.

A5. The method of clause A1, wherein the transducer element specific kernels are generated by the steps comprising:
  estimating an impulse response for each transducer element;
  filtering the estimated impulse responses based upon prior transducer element knowledge; and
  applying 1-dimensional noise and artifact reduction to the filtered estimated impulse responses.

A6. The method of clause A5, wherein the prior transducer element knowledge is selected from the group consisting of a bandwidth of each transducer in the thermoacoustic imaging system, a center frequency of each transducer in the thermoacoustic imaging system, a value derived from a noise test, or some combination thereof.

A7. A thermoacoustic imaging system configured to reconstruct a thermoacoustic tomography image, the system comprising:
- a radio-frequency source configured to direct pulses of radio-frequency electromagnetic radiation toward a region of interest and induce thermoacoustic signals from the region of interest;
- at least one thermoacoustic transducer configured to receive the thermoacoustic signals from the region of interest; and
- a processor configured to accept data from the radio-frequency source and the at least one thermoacoustic transducer, wherein the processor is further configured to record time-series data for each respective transducer in the thermoacoustic imaging system, deconvolve transducer element specific kernels for each respective transducer in the thermoacoustic imaging system, filter with a time domain reconstruction filter and then back-project to generate at least one back-projected image, and spatially combine the least one back-projected image to generate a reconstructed image.

A8. The system of clause A7, wherein the processor is further configured to denoise and correct with algorithms to generate corrected time-series data for each transducer, immediately after recording time-series data for each respective transducer in the thermoacoustic imaging system.

A9. The system of clause A8, wherein the processor is further configured to apply two-dimensional denoising and artifact correction algorithms to generate corrected deconvolved time-series data, immediately after deconvolving transducer element specific kernels for each respective transducer in the thermoacoustic imaging system.

A10. The system of clause A7, wherein the processor is further configured to apply two-dimensional denoising and artifact correction algorithms to generate corrected deconvolved time-series data, immediately after deconvolving transducer element specific kernels for each respective transducer in the thermoacoustic imaging system.

A11. The system of clause A7, wherein the processor is further configured to generate the transducer element specific kernels by the steps comprising:
- estimating an impulse response for each transducer element;
- filtering the estimated impulse responses based upon prior transducer element knowledge; and
- applying 1-dimensional noise and artifact reduction to the filtered estimated impulse responses.

A12. The system of clause A11, wherein the prior transducer element knowledge is selected from the group consisting of a bandwidth of each transducer in the thermoacoustic imaging system, a center frequency of each transducer in the thermoacoustic imaging system, a value derived from a noise test, or some combination thereof.

B1. A method of thermoacoustic tomography image reconstruction that utilizes a thermoacoustic imaging system, the method comprising:
- recording time-series data for each respective transducer in the thermoacoustic imaging system;
- deconvolving transducer element specific kernels for each respective transducer in the thermoacoustic imaging system;
- applying 2-D denoising and artifact correction algorithms to generate corrected deconvolved time-series data;
- backprojecting to generate an image for each view and impulse position;
- applying a view and position specific n-dimensional image kernel;
- combining for all available views; and
- spatially combining to generate a reconstructed image.

B2. The method of clause B1, further comprising denoising and correcting with algorithms to generate corrected time-series data for each transducer, immediately after the recording step.

B3. The method of clause B1, wherein the view and position specific n-dimensional image kernel is generated by the steps comprising:
- generating a thermoacoustic impulse at a known position within a field of view;
- recording time-series data for each transducer in the thermoacoustic imaging system;
- applying one-dimensional noise and artifact reduction to the time-series data based upon a prior knowledge;
- collecting thermoacoustic data from the transducers in the thermoacoustic imaging system; and
- applying a back projection to the collected thermoacoustic data to generate the view and position specific n-dimensional image kernel.

B4. The method of clause B3, wherein the prior knowledge is selected from the group consisting of a bandwidth of each transducer in the thermoacoustic imaging system, a center frequency of each transducer in the thermoacoustic imaging system, a value derived from a noise test, or some combination thereof.

B5. A thermoacoustic imaging system configured to reconstruct a thermoacoustic tomography image, the system comprising:
- a radio-frequency source configured to direct pulses of radio-frequency electromagnetic radiation toward a region of interest and induce thermoacoustic signals from the region of interest;
- at least one thermoacoustic transducer configured to receive the thermoacoustic signals from the region of interest; and
- a processor configured to accept data from the radio-frequency source and the at least one thermoacoustic transducer, wherein the processor is further configured to record time-series data for each respective transducer in the thermoacoustic imaging system, deconvolve transducer element specific kernels for each respective transducer in the thermoacoustic imaging system, apply 2-D denoising and artifact correction algorithms to generate corrected deconvolved time-series data, backproject to generate an image for each view and impulse position, apply a view and position specific n-dimensional image kernel, combine for all available views; and spatially combine to generate a reconstructed image.

B6. The system of clause B5, wherein the processor is further configured to denoise and correct with algorithms to generate corrected time-series data for each transducer, immediately after recording time-series data for each respective transducer in the thermoacoustic imaging system.

B7. The system of clause B5, wherein the view and position specific n-dimensional image kernel is generated by the steps comprising:
- generating a thermoacoustic impulse at a known position within a field of view;

recording time-series data for each transducer in the thermoacoustic imaging system;

applying one-dimensional noise and artifact reduction to the time-series data based upon a prior knowledge;

collecting thermoacoustic data from the transducers in the thermoacoustic imaging system; and applying a back projection to the collected thermoacoustic data to generate the view and position specific n-dimensional image kernel.

B8. The system of clause B7, wherein the prior knowledge is selected from the group consisting of a bandwidth of each transducer in the thermoacoustic imaging system, a center frequency of each transducer in the thermoacoustic imaging system, a value derived from a noise test, or some combination thereof.

C1. A method of thermoacoustic tomography image reconstruction that utilizes a thermoacoustic imaging system, the method comprising:

recording time-series data for each respective transducer in the thermoacoustic imaging system;

deconvolving transducer element specific kernels for each respective transducer in the thermoacoustic imaging system;

applying 2-D denoising and artifact correction algorithms to generate corrected deconvolved time-series data;

backprojecting to generate an image for each view and impulse position;

combining the image for each view and impulse position;

applying a position specific volume kernel; and spatially combining to generate a reconstructed image.

C2. The method of clause C1, further comprising denoising and correcting with algorithms to generate corrected time-series data for each transducer, immediately after the recording step.

C3. The method of clause C1, wherein the position specific volume kernel is generated by the steps comprising:

generating a thermoacoustic impulse at a known position within a field of view;

recording time-series data for each transducer in the thermoacoustic imaging system;

applying one-dimensional noise and artifact reduction to the time-series data based upon a prior knowledge;

collecting thermoacoustic data from the transducers in the thermoacoustic imaging system;

applying a back projection to the collected thermoacoustic data to generate the view and position specific n-dimensional image kernel; and repeating the generating, recording, applying one-dimensional noise and artifact reduction, collecting, and applying back projection steps for all available views and combining results to obtain the position specific volume kernel.

C4. The method of clause C3, wherein the prior knowledge is selected from the group consisting of a bandwidth of each transducer in the thermoacoustic imaging system, a center frequency of each transducer in the thermoacoustic imaging system, a value derived from a noise test, or some combination thereof.

C5. A thermoacoustic imaging system configured to reconstruct a thermoacoustic tomography image, the system comprising:

a radio-frequency source configured to direct pulses of radio-frequency electromagnetic radiation toward a region of interest and induce thermoacoustic signals from the region of interest;

at least one thermoacoustic transducer configured to receive the thermoacoustic signals from the region of interest; and a processor configured to accept data from the radio-frequency source and the at least one thermoacoustic transducer, wherein the processor is further configured to record time-series data for each respective transducer in the thermoacoustic imaging system, deconvolve transducer element specific kernels for each respective transducer in the thermoacoustic imaging system, apply 2-D denoising and artifact correction algorithms to generate corrected deconvolved time-series data, backproject to generate an image for each view and impulse position, combine the image for each view and impulse position, apply a position specific volume kernel, and spatially combine to generate a reconstructed image.

C6. The system of clause C5, wherein the processor is further configured to denoise and correct with algorithms to generate corrected time-series data for each transducer, immediately after recording time-series data for each respective transducer in the thermoacoustic imaging system.

C7. The system of clause C5, wherein the position specific volume kernel is generated by the steps comprising:

generating a thermoacoustic impulse at a known position within a field of view;

recording time-series data for each transducer in the thermoacoustic imaging system;

applying one-dimensional noise and artifact reduction to the time-series data based upon a prior knowledge;

collecting thermoacoustic data from the transducers in the thermoacoustic imaging system;

applying a back projection to the collected thermoacoustic data to generate the view and position specific n-dimensional image kernel; and repeating the generating, recording, applying one-dimensional noise and artifact reduction, collecting, and applying back projection steps for all available views and combining results to obtain the position specific volume kernel.

C8. The system of clause C7, wherein the prior knowledge is selected from the group consisting of a bandwidth of each transducer in the thermoacoustic imaging system, a center frequency of each transducer in the thermoacoustic imaging system, a value derived from a noise test, or some combination thereof.

Although embodiments have been described above with reference to the accompanying drawings, those of skill in the art will appreciate that variations and modifications may be made without departing from the scope thereof as defined by the appended claims.

What is claimed is:

1. A method for reconstructing a thermoacoustic image comprising:

directing radio frequency (RF) energy pulses generated by an RF source into a tissue region of interest;

detecting, at each of a plurality of views along a scanning trajectory of a transducer element array about the region of interest, acoustic signals generated within the region of interest in response to the RF energy pulses and generating thermoacoustic data;

applying at least one correction kernel to the thermoacoustic data, wherein the at least one correction kernel is a view and position specific kernel to correct for differences in the relative relationship between the transducer element array and an object within the region of interest to be imaged at each view, further wherein the view and position specific kernel for a selected view is generated by:
(i) generating an acoustic impulse at a known impulse position within a field of view of the transducer element array;
(ii) recording time-series thermoacoustic data for each transducer element of the transducer element array;
(iii) combining the thermoacoustic data recorded for each transducer element to generate a matrix; and
(iv) applying back projection to the matrix to generate the view and position specific kernel; and
after the at least one correction kernel has been applied to the thermoacoustic data, reconstructing a thermoacoustic image therefrom.

2. The method of claim 1, wherein the at least one correction kernel is generated during a calibration procedure.

3. The method of claim 1, wherein the at least one correction kernel is a transducer element specific kernel to correct for different properties of individual transducer elements of the array.

4. The method of claim 3, wherein the transducer element specific kernel is generated by:
(i) estimating an impulse response of each transducer element of the array;
(ii) applying a filter to the impulse responses based on one or more known unique characteristics of the transducer elements; and
(iii) applying a noise and artifact correction to the filtered impulse responses.

5. The method of claim 4, wherein the one or more known unique characteristics comprise at least one of center frequency, bandwidth and noise sensitivity.

6. The method of claim 1, wherein the at least one kernel is a position specific volume kernel to correct for variations in spatial sensitivity as a result of transducer element array and scanning geometries.

7. The method of claim 6, wherein the position specific volume kernel is generated by:
(i) generating an acoustic impulse at a known impulse position within a field of view of the transducer element array;
(ii) recording time-series thermoacoustic data for each transducer element of the transducer element array;
(iii) combining the thermoacoustic data recorded for each transducer element to generate a matrix;
(iv) applying back projection to the matrix to generate a view and position specific kernel;
(v) repeating steps (i) to (iv) for each view of the transducer element array; and
(vi) repeating steps (i) to (v) for each known impulse position within the field of view.

8. The method of claim 1, wherein multiple correction kernels are applied to the thermoacoustic data.

9. The method of claim 8, wherein the correction kernels comprise a transducer element specific kernel to correct for different properties of individual transducer elements of the array and a view and position specific kernel to correct for differences in the relative relationship between the transducer element array and an object within the region of interest to be imaged at each view.

10. The method of claim 8, wherein the correction kernels comprise a transducer element specific kernel to correct for different properties of individual transducer elements of the array and a position specific volume kernel to correct for variations in spatial sensitivity as a result of transducer element array and scanning geometries.

11. The method of claim 1, wherein the scanning trajectory is circular or non-circular.

12. The method of claim 1 further comprising applying a noise and artifact correction algorithm to the thermoacoustic data prior to reconstructing the thermoacoustic image.

13. A thermoacoustic imaging system comprising:
a radio frequency source configured to emit RF pulses into a region of interest and heat tissue therein;
a transducer element array moveable along a scanning trajectory about the region of interest and configured to receive acoustic signals generated in response to heating of the tissue, at each of a plurality of views along the scanning trajectory, and generate thermoacoustic data; and
one or more processors configured to:
apply an at least one correction kernel to the thermoacoustic data, wherein the at least one correction kernel is a view and position specific kernel to correct for differences in the relative relationship between the transducer element array and an object within the region of interest to be imaged at each view, further wherein the view and position specific kernel for a selected view is generated by:
(i) generating an acoustic impulse at a known impulse position within a field of view of the transducer element array;
(ii) recording time-series thermoacoustic data for each transducer element of the transducer element array;
(iii) combining the thermoacoustic data recorded for each transducer element to generate a matrix; and
(iv) applying back projection to the matrix to generate the view and position specific kernel; and
reconstruct a thermoacoustic image after the at least one correction kernel has been applied to the thermoacoustic data.

14. A method of calibrating a thermoacoustic imaging system comprising a transducer element array that includes a plurality of transducer elements and that is moved along a scanning trajectory about a region of interest during thermoacoustic imaging to detect acoustic signals induced within the region of interest at a plurality of views along the scanning trajectory, the method comprising:
applying an at least one correction kernel to the thermoacoustic data, wherein the at least one correction kernel is a view and position specific kernel to correct for differences in the relative relationship between the transducer element array and an object within the region of interest to be imaged at each view, further wherein the view and position specific kernel for a selected view is generated by:
(i) generating an acoustic impulse at a known impulse position within a field of view of the transducer element array;
(ii) recording time-series thermoacoustic data for each transducer element of the transducer element array;
(iii) combining the thermoacoustic data recorded for each transducer element to generate a matrix; and
(iv) applying back projection to the matrix to generate the view and position specific kernel; and
storing the at least one kernel in memory for use by one or more processors during thermoacoustic image reconstruction.

15. The method of claim 14, wherein the transducer element specific kernel is generated by:
(i) estimating an impulse response of each transducer element of the array;

(ii) applying a filter to the impulse responses based on one or more known unique characteristics of the transducer elements; and
(iii) applying a noise and artifact correction to the filtered impulse responses.

16. The method of claim 14, wherein the position specific volume kernel is generated by:
(i) generating an acoustic impulse at a known impulse position within a field of view of the transducer element array;
(ii) recording time-series thermoacoustic data for each transducer element of the transducer element array;
(iii) combining the thermoacoustic data recorded for each transducer element to generate a matrix;
(iv) applying back projection to the matrix to generate a view and position specific kernel;
(v) repeating steps (i) to (iv) for each view of the transducer element array; and
(vi) repeating steps (i) to (v) for each known impulse position within the field of view.

* * * * *